US00PP22411P2

(12) United States Plant Patent
Dümmen

(10) Patent No.: US PP22,411 P2
(45) Date of Patent: Dec. 27, 2011

(54) ***PELARGONIUM* PLANT NAMED 'DUESABU'**

(50) Latin Name: *Pelargonium zonale*
Varietal Denomination: Duesabu

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/928,563

(22) Filed: Dec. 14, 2010

(51) Int. Cl.
*A01H 5/00* (2006.01)

(52) U.S. Cl. ..... Plt./329

(58) Field of Classification Search ..... Plt./329
See application file for complete search history.

*Primary Examiner* — Kent L Bell

(74) *Attorney, Agent, or Firm* — C. A. Whealy

(57) ABSTRACT

A new and distinct cultivar of Zonal Geranium plant named 'Duesabu', characterized by its upright to outwardly spreading plant habit; vigorous growth habit; freely basal branching habit; leaves with a distinct zonation pattern; freely flowering habit; semi-double red purple-colored flowers; and good garden performance.

1 Drawing Sheet

Botanical designation: *Pelargonium zonale.*
Cultivar denomination: 'DUESABU'.

BACKGROUND OF THE INVENTION

The present invention relates to a new and distinct cultivar of Zonal Geranium plant, botanically known as *Pelargonium zonale* and hereinafter referred to by the name 'Duesabu'.

The new Zonal Geranium plant is a product of a planned breeding program conducted by the Inventor in Rheinberg, Germany. The objective of the breeding program is to create new uniform Zonal Geranium plants with dark green-colored leaves and attractive flowers.

The new Zonal Geranium plant originated from a cross-pollination made by the Inventor in May, 2005 in Rheinberg, Germany of a proprietary selection of *Pelargonium zonale* identified as code number F-02-01, not patented, as the female, or seed, parent with a proprietary selection of *Pelargonium zonale* identified as code number Z98-1216-001, not patented, as the male, or pollen, parent. The new Zonal Geranium plant was discovered and selected by the Inventor as a single flowering plant from within the progeny of the stated cross-pollination in a controlled greenhouse environment in Rheinberg, Germany in May, 2008.

Asexual reproduction of the new Zonal Geranium plant by vegetative terminal cuttings in a controlled greenhouse environment in Rheinberg, Germany since May, 2008 has shown that the unique features of this new Zonal Geranium plant are stable and reproduced true to type in successive generations.

SUMMARY OF THE INVENTION

Plants of the new Zonal Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesabu'. These characteristics in combination distinguish 'Duesabu' as a new and distinct Zonal Geranium plant:

1. Upright to outwardly spreading plant habit.
2. Vigorous growth habit.
3. Freely basal branching habit.
4. Leaves with a distinct zonation pattern.
5. Freely flowering habit.
6. Semi-double red purple-colored flowers.
7. Good garden performance.

Plants of the new Zonal Geranium differ primarily from plants of the female parent selection in growth habit as plants of the new Zonal Geranium are more vigorous than plants of the female parent selection. In addition, plants of the new Zonal Geranium and the female parent selection differ in flower color.

Plants of the new Zonal Geranium differ primarily from plants of the male parent selection in growth habit as plants of the new Zonal Geranium are not as vigorous as plants of the male parent selection. In addition, plants of the new Zonal Geranium have darker green-colored leaves than plants of the male parent selection.

Plants of the new Zonal Geranium can be compared to plants of *Pelargonium zonale* 'Fip 750', disclosed in U.S. Plant Pat. No. 14,011. In side-by-side comparisons conducted in Rheinberg, Germany plants of the new Zonal Geranium differed primarily from plants of 'Fip 750' in the following characteristics:

1. Plants of the new Zonal Geranium were more vigorous than plants of 'Fip 750'.
2. Leaves of plants of the new Zonal Geranium were broader and had a more distinct zonation pattern than leaves of plants of 'Fip 750'.
3. Plants of the new Zonal Geranium had larger flowers than plants of 'Fip 750'.
4. Plants of the new Zonal Geranium and 'Fip 750' differed in flower color as plants of 'Fip 750' had purple violet-colored flowers.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Duesabu' grown in a container.

DETAILED BOTANICAL DESCRIPTION

The aforementioned photograph and following observations and measurements describe plants grown during the summer in 10.5-cm containers in a glass-covered greenhouse in Rheinberg, Germany and under conditions which closely approximate commercial production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duesabu'.

Parentage:

*Female, or seed, parent.*—Proprietary selection of *Pelargonium zonale* identified as code number F-02-01, not patented.

*Male or pollen parent.*—Proprietary selection of *Pelargonium zonale* identified as code number Z98-1216-001, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*General appearance.*—Upright to outwardly spreading plant habit; uniformly rounded; densely foliated.

*Growth and branching habit.*—Vigorous growth habit; freely basal branching habit with about three basal branches developing per plant; pinching enhances lateral branch development.

*Plant height to top of flower umbels.*—About 22 cm.

*Plant height to top of foliar plane.*—About 19 cm.

*Plant width.*—About 20 cm.

*Lateral branches.*—Length: About 6 cm. Diameter: About 8 mm. Internode length: About 2.3 cm. Texture: Pubescent. Strength: Moderately strong. Color: Close to 144C.

Foliage description:

*Arrangement.*—Alternate; simple.

*Length.*—About 4.3 cm.

*Width.*—About 7.6 cm.

*Shape.*—Reniform.

*Apex.*—Acute.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing leaves, upper surface: Close to 137A. Developing leaves, lower surface: Close to 138B. Fully expanded leaves, upper surface: Close to 137A; venation, close to 143B. Fully expanded leaves, lower surface: Close to 137C; venation, close to 144C.

*Zonation pattern.*—Distinct. Distance from margin: About 1.5 cm. Width: About 1.5 cm. Color: Close to 136B.

*Petiole.*—Length: About 4.5 cm. Diameter: About 3.5 mm. Texture, upper and lower surfaces: Smooth, glabrous. Color, upper surface: Close to 144A. Color, lower surface: Close to 144C.

Flower description:

*Flower arrangement.*—Semi-double flowers arranged in rounded hemispherical umbels arising from apical leaf axils; umbels displayed above the foliage on moderately strong peduncles; flowers face mostly upright to outward.

*Fragrance.*—None detected.

*Quantity of flowers.*—Freely flowering habit; about 20 flowers and flower buds per umbel with about 110 flowers per plant.

*Flowering season.*—Year-round under greenhouse conditions; in outdoor nurseries and gardens in Germany flowering is continuous from spring throughout the summer; plants begin flowering about eight weeks after planting.

*Flower longevity.*—Individual flowers last about five to seven days on the plant; flowers persistent.

*Umbel height.*—About 6 cm.

*Umbel diameter.*—About 7.3 cm.

*Flower diameter.*—About 5 cm by 5.4 cm.

*Flower depth (height).*—About 2.1 cm.

*Flower buds.*—Length: About 1.3 cm. Diameter: About 7.2 mm. Shape: Ovoid. Color: Close to 67A.

*Petals.*—Quantity per flower: About five in a single whorl. Length: About 2.8 cm. Width: About 2 cm. Shape: Obovate. Apex: Rounded. Base: Attenuate. Margin: Sinuate. Texture, upper and lower surfaces: Smooth, glabrous. Color: When opening, upper surface: Close to 66A; towards the base, close to 62D. When opening, lower surface: Close to 67C to 67D. Fully opened, upper surface: Close to 66A; towards the base, close to 62D; color becoming closer to 67C to 67D with development. Fully opened, lower surface: Close to 57C to 57D; color becoming closer to 67A to 67B with development.

*Petaloids.*—Quantity per flower: About four to seven. Length: About 1.8 cm. Width: About 1.4 cm. Shape: Obovate. Apex: Rounded. Base: Attenuate. Margin: Sinuate. Texture, upper and lower surfaces: Smooth, glabrous. Color: When opening, upper surface: Close to 66A; towards the base, close to 62D. When opening, lower surface: Close to 67C to 67D. Fully opened, upper surface: Close to 66A; towards the base, close to 62D. Fully opened, lower surface: Close to 57C to 57D.

*Sepals.*—Quantity per flower: About five arranged in a single whorl. Length: About 1.1 cm. Width: About 3.75 mm. Shape: Ensiform. Apex: Acuminate. Base: Acute. Margin: Entire. Texture, upper and lower surfaces: Smooth, glabrous. Color, upper and lower surfaces: Close to 143B tinted with close to 53B.

*Peduncle* (*umbel stem*).—Length: About 14 cm. Diameter: About 4.5 mm. Strength: Moderately strong. Texture: Smooth, glabrous. Color: Close to 144A.

*Pedicel* (*individual flower stem*).—Length: About 2.6 cm. Diameter: About 1.5 mm. Strength: Moderately strong. Texture: Smooth, glabrous. Color: Close to 180B.

*Reproductive organs.*—Androecium: Stamen quantity per flower: About nine. Filament length: About 7 mm. Filament color: Close to 155C. Anther length: About 2 mm. Anther shape: Oval. Anther color: Close to 61B. Pollen amount: Moderate. Pollen color: Close to 28A. Gynoecium: Pistil quantity per flower: One. Pistil length: About 9 mm. Stigma shape: Parted. Stigma color: Close to 45B. Style length: About 2 mm. Style color: Close to 44C. Ovary color: Close to 144A.

*Seed/fruit.*—Seed and fruit development have not been observed.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind, and temperatures ranging from about 5° C. to about 40° C. and have demonstrated good garden performance.

It is claimed:

1. A new and distinct Zonal Geranium plant named 'Duesabu' as illustrated and described.

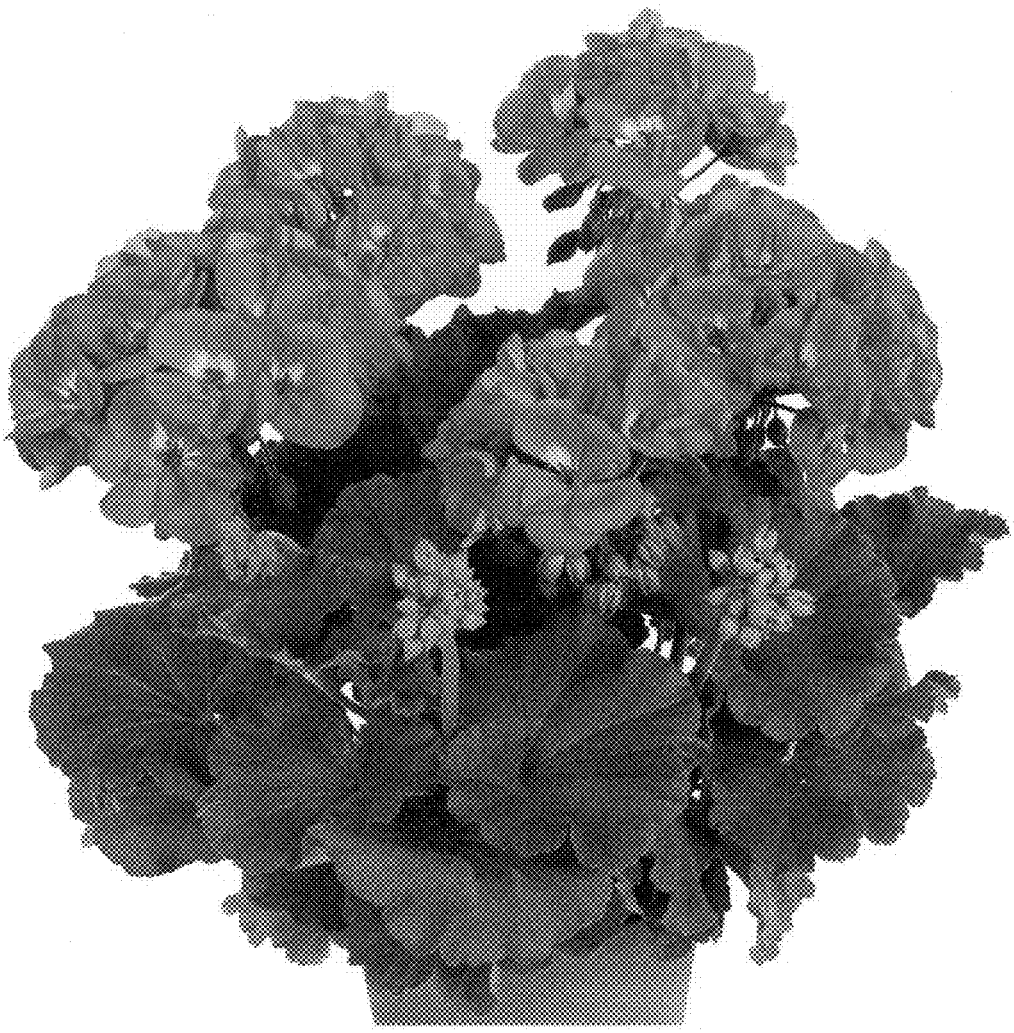

* * * * *